(12) United States Patent
Canady

(10) Patent No.: US 6,367,427 B1
(45) Date of Patent: Apr. 9, 2002

(54) SHIELD AND TRANSPORT APPARATUS

(76) Inventor: Duane C. Canady, 6435 W. Christy La., Glendale, AZ (US) 85304

( * ) Notice: Subject to any disclaimer, the term of this patent is extended or adjusted under 35 U.S.C. 154(b) by 0 days.

(21) Appl. No.: 09/541,656

(22) Filed: Apr. 3, 2000

(51) Int. Cl.[7] .......................... A62B 35/00; A60R 22/00; A60R 22/12; A61G 7/08
(52) U.S. Cl. ...................... 119/857; 5/81.1 R; 5/81.1 C; 5/81.1
(58) Field of Search ................................. 119/856, 857, 119/850; 5/81 R, 88.1, 89.1, 81.1 C, 81.1 RP, 81.1 HS, 81.1 T

(56) References Cited

U.S. PATENT DOCUMENTS

| | | | | |
|---|---|---|---|---|
| 1,173,459 A | * | 2/1916 | Palmer | 5/81 R |
| 2,480,314 A | * | 8/1949 | Benedict | 5/81 R |
| 3,469,268 A | * | 9/1969 | Phillips | 5/81 R |
| 4,716,607 A | * | 1/1988 | Johansson | 5/81 R |
| 4,744,115 A | * | 5/1988 | Marchione | 5/81 R |
| 5,577,281 A | * | 11/1996 | Mital et al. | 5/81 R |
| 5,839,137 A | * | 11/1998 | Butler et al. | 5/627 |
| 5,966,754 A | * | 10/1999 | Schuster | 5/81 R |
| 6,006,700 A | * | 12/1999 | Cox | 119/857 |

* cited by examiner

Primary Examiner—Charles T. Jordan
Assistant Examiner—Judith A. Nelson
(74) Attorney, Agent, or Firm—H. Gordon Shields

(57) ABSTRACT

Shield and transport apparatus includes a pair of panels secured together which may by used as a shield while a person or persons are advancing towards a combative person in which may be partially wrapped around the combative person to help restrain the person. The apparatus may then be used to transport the combative person after the person is subdued. The apparatus is impervious to moisture and is padded for protection and is somewhat rigid enough for transport purposes and is flexible so that it may be disposed about a person being subdued.

6 Claims, 1 Drawing Sheet

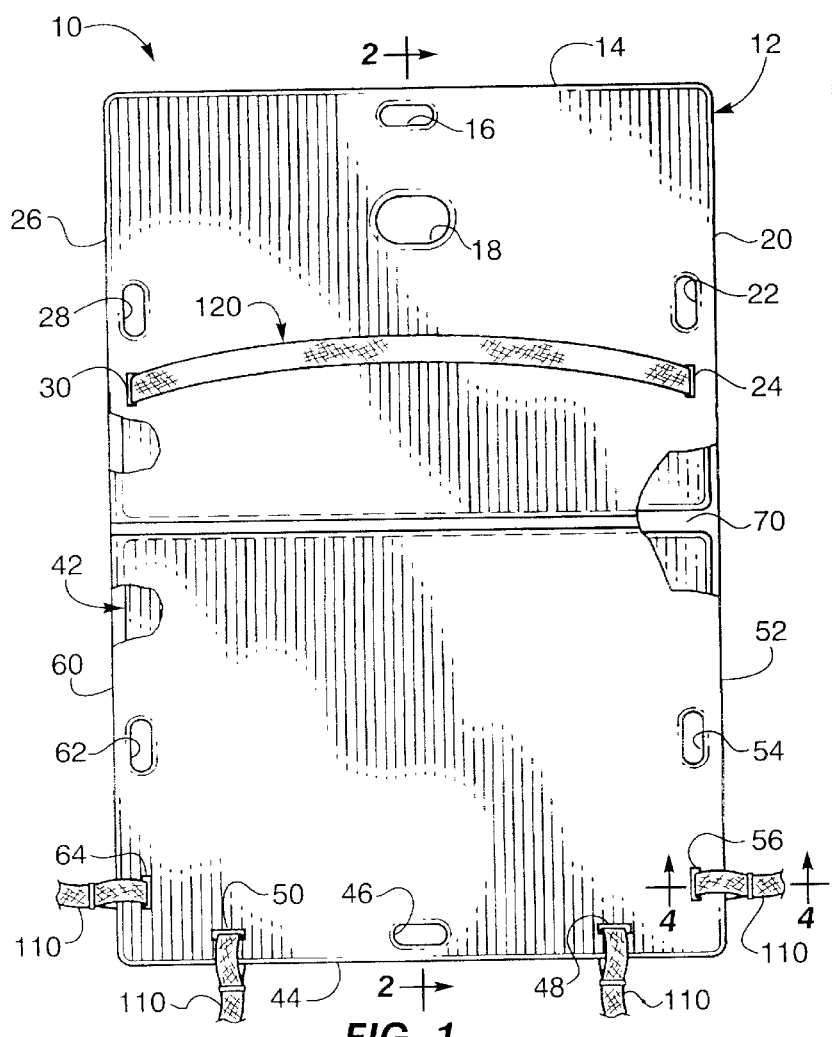
FIG. 1.
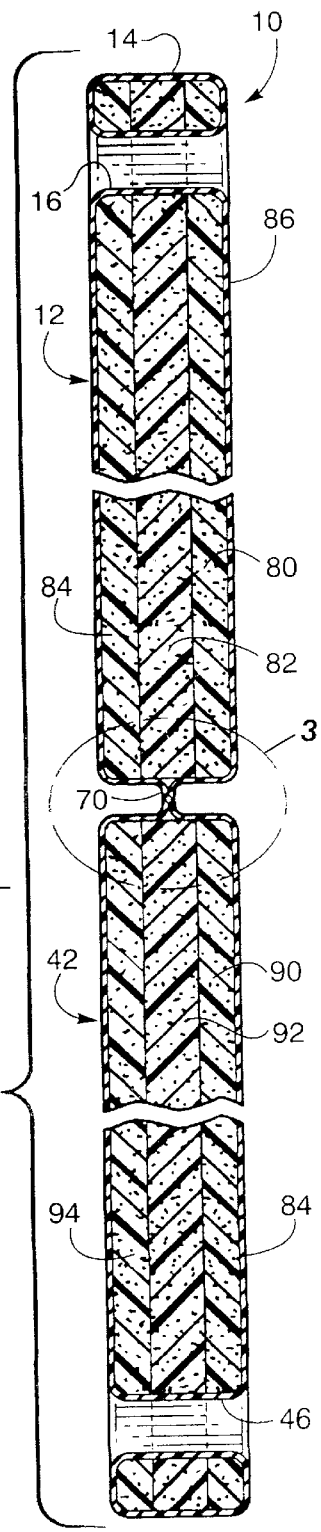
FIG. 2.
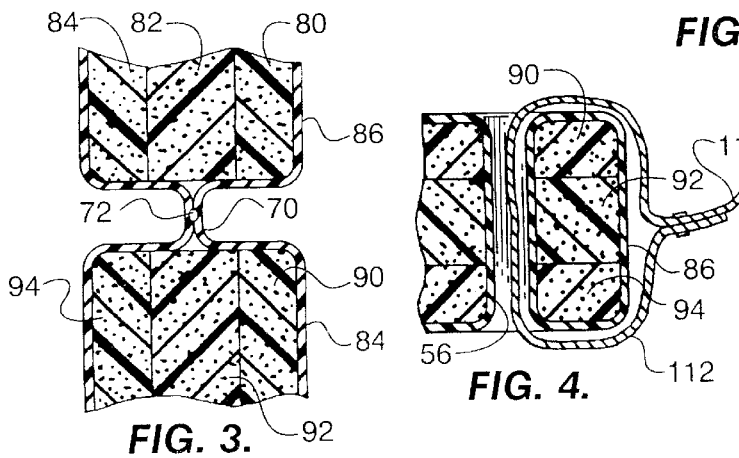
FIG. 3.
FIG. 4.

SHIELD AND TRANSPORT APPARATUS

BACKGROUND OF THE INVENTION

1. Field of the Invention

This invention relates to apparatus for shielding a person from a combative person and for transporting the combative person after the person has been subdued.

2. Description of the Prior Art

A continuous problem with combative persons, such as different types of psychiatric patients, has been the ability to subdue the person with minimal damage to both the person being subdued and the caretakers subduing the person. A further problem has been then to transport the subdued person to the appropriate facility. Typically, the combative person is simply overpowered or overwhelmed by a number of persons by sheer physical force. Combative persons have been known to pick up different kinds of objects and throw them at the would-be subduers, and to fight with hands and feet in resisting the subduers. The transporting may be simply physically picking the subdued person up and physically carrying the individual. On the other hand, if the subdued person is sedated, a wheel chair or a gurney may be used to transport the person.

There are obvious disadvantages to the crude methods used heretofore in which the present invention overcomes.

The present invention provides a simple yet very effective shield behind which subduers may advance on the combative person and which may be used to help subdue the individual. The apparatus may then be used as a stretcher, or the like, on which the subdued person may be transported. The apparatus includes provisions for restraining the individual while the individual is being transported.

SUMMARY OF THE INVENTION

The invention described and claimed herein comprises a combination shield and stretcher for subduing a combative person and for transporting the combative person after the person is subdued. The apparatus comprises a two portion shield which folds in the middle and which may be used to wrap partially around a person to help subdue the person. Appropriate apertures or holes extend through the apparatus for hand holds and include apertures for securing restraints to the elements and an aperture through which a subduer may look while yet being protected and which aperture may be used to receive the face of the individual subdued when the individual is placed face down on the apparatus for transport purposes. The apparatus includes a moisture impervious outer covering enclosing a padded and yielding, and yet somewhat inflexible interior such that the apparatus may be used as both a shield and a transport carrier on which an individual may be placed for transport purposes.

Among the objects of the present invention are the following:

To provide new and useful shield apparatus for protecting a person against a combative individual;

To provide new and useful apparatus on which a person may be disposed for transport purposes;

To provide new and useful shield apparatus which may be disposed about a combative person to help subdue the person;

To provide new and useful transport apparatus having a plurality of restraint elements for restraining a person being subdued; and To provide new and useful shield and transport apparatus for protecting individuals as they advance on a combative person and for transporting the combative person after the combative person has been subdued.

BRIEF DESCRIPTION OF THE DRAWING

FIG. 1 is a plan view of the apparatus of the present invention.

FIG. 2 is a view in partial section taken generally along line 2—2 of FIG. 1.

FIG. 3 is a view in partial section taken generally from oval 3 of FIG. 2.

FIG. 4 is a view in partial section taken generally along line 4—4 of FIG. 1.

DESCRIPTION OF THE PREFERRED EMBODIMENT

FIG. 1 is a plan view of shield and transport apparatus 10 of the present invention. The apparatus includes two portions, an upper portion 12 and a lower portion 42 joined by a hinge portion 70. The portions 12 and 42 comprise a pair of semi-rigid panels connected together by the hinge portion 70. FIG. 2 is a view in partial section through the apparatus 10 taken generally along line 2—2 of FIG. 1, showing the construction of the apparatus and, in general, the two portions 12 and 42. FIG. 3 is an enlarged view in partial section taken generally from oval 3 of FIG. 2, illustrating the hinge 70 and the elements of the apparatus 10 located in the area of a weld 72, namely the juncture of the two portions, the upper portion 12 and the lower portion 42.

FIG. 4 is an enlarged view in partial section taken generally along line 4—4, illustrating the feature of the apparatus of the present invention. For the following discussion, reference will be made to all four of the drawing Figures.

The upper portion 12 and the lower portion 42 are generally of a rectangular configuration and are generally of the same size and construction. The two portions differ only in details. The two portions 12 and 42 are disposed adjacent to and aligned with each other. They are joined by a hinge, as will be described below.

The upper portion 12 includes a top edge 14 and a pair of side edges 20 and 26. Downwardly from the top edge 14, and located centrally between the side edges 20 and 26 is a hand hold slot 16. Spaced downwardly from the hand hold slot 16 is a head aperture 18.

Spaced inwardly from the side edge 20 a relatively short distance is another hand hold slot 22. A similar hand slot 28 is disposed inwardly from the side edge 26. The slots 22 and 28 are generally aligned with each other.

Spaced downwardly from the hand hold 22, and again inwardly from the side edge 20, is a strap aperture or hole. Aligned with the strap aperture or hole 24 is another strap aperture of slot 30. The slot 30 is spaced inwardly a slight distance from the side edge 26.

The lower portion 52 includes a pair of side edges 52 and 60 and a bottom edge 44. Spaced inwardly from the side edge 52 is a hand hold slot 54. Spaced inwardly from the side edge 60 is another hand hold slot 62. The slots 54 and 62 are generally aligned with each other.

Spaced apart upwardly from the bottom edge 44 is a hand hold slot 46. A pair of strap apertures or holes 48 and 50 are spaced apart from each other, and from the slot 46, and are disposed upwardly from the bottom edge 44. Another pair of strap apertures or holes 56 and 64 are aligned with each other and spaced inwardly from the side edges 52 and 60, respectively, and spaced upwardly from the bottom edge 44. The strap apertures or slots 56 and 64 are also generally aligned with each other.

In construction, the apparatus 10 includes three semi-rigid layers of foam padding 80, 82, and 84 in the upper portion 12, and three similar semi-rigid layers of foam padding 90, 92, and 84 in the lower portion 42. The three layers in both the upper portions 12 and the lower portion 42 may be bonded together, if desired. The three layers define a semi-rigid upper panel 12 and a semi-rigid lower panel 42.

An outer cover 86 is disposed entirely about the foam layers in both the upper and lower panels. As best shown in FIG. 3, at the hinge 70 the outer layer 86 is welded to itself. The weld is indicated by a reference numeral 72 in FIG. 3. Thus, the hinge 70 comprises, essentially, a living hinge in which the outer layer 86 is welded to itself The hinge 70 connects the upper portion or panel 12 and the lower portion or panel 42 together.

As indicated in both FIGS. 2 and 4, the hand hold slots and the strap apertures or slots are essentially fully enclosed by the outer layer or cover 86.

FIG. 4 discloses a strap 110 extending through the strap aperture or slot 56. A loop 112 may be conveniently formed in the strap 110 by use of hook and loop fasteners, details of which are not illustrated, but are well known and understood.

Other straps 110 are illustrated in FIG. 1 extending through the strap holes or apertures 48, 50, and 64. A relatively large strap 120 is shown in FIG. 1 extending between the strap slots 24 and 30 in the upper portion 12. The strap 120 may also, like the other straps, use hook and loop fasteners, not shown. The strap 120 may be conveniently secured on the bottom or reverse side of the panel 12, if desired. The strap 120 is a chest strap, designed to fit over the chest portion or upper torso of a patient.

Obviously, there may be as many restraint straps as desired or as needed to restrain a combative patient. In different sized apparatus, the straps may be located in different areas of the panels.

In use, the apparatus 10 may be used to approach an unruly or combative patient, with the apparatus 10 held in an upright position by the hand holes 22 and 28. The user of the apparatus 10 may look through the head aperture 18 when approaching the unruly and combative patient. The overall length, between the top edge 14 and the bottom edge 44 may be as desired, but typically should be about six feet or so. The width is illustrated as being substantially larger than half the length, and may conveniently be sized approximately two-thirds of the overall length of the apparatus. For example, if the apparatus 10 were to have an overall length of about six feet, the overall width between the sides 22, 52, 26 and 60, would be about four feet. The exact dimensions may, of course, vary, and, the shield and transport apparatus 10 may be made in various dimensions, depending on the type of patient with which an apparatus 10 will be used.

With the apparatus being made of semi-rigid panels, the apparatus may be relatively easily contoured about a combative person, and then straps may be used to secure the person to the apparatus 10, and the apparatus 10 is then converted into a transport pallet for transporting the patient to an appropriate area.

In the transport mode, the head aperture or hole 18 receives a portion of the patient's head, and the various strap apertures or slots are used to receive straps to hold a patient to the apparatus 10. Very conveniently, up to about six people may be used to carry a patient on the apparatus 10 by use of the hand hold slots 16, 22, 54, 46, 62, and 28. Obviously, for a relatively small or light patient, only two attendants will be needed. Thus, the slots 22 and 54, spaced inwardly from the sides 20 and 52 of the upper and lower panels 20 and 42, respectively, are spaced apart a distance such that a single person may grasp both of the slots. Similarly, a single person may grasp the slots 28 and 62 of the upper and lower portions sides 26 and 60, respectively.

While the restraint straps are illustrated as extending through holes or apertures at the periphery of the panels, it is obvious that they may also be sewn to the panels, if desired.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Shield and transport apparatus comprising in combination:

a first semi-rigid panel having a first plurality of edges;

a second semi-rigid panel having a second plurality of edges disposed adjacent to and aligned with the first panel;

hinge means for connecting the first and second panels;

a head aperture in the first panel for receiving the head of a patient;

a plurality of hand holds spaced apart from each other along the first and second plurality of edges for carrying a person secured to the apparatus; and means for securing a patient to the first and second panels, including a plurality of slots and restraint straps extending through the slots for securing patient's heads and feet.

2. The apparatus of claim 1 which further includes a covering for the first and second panels.

3. The apparatus of claim 2 in which the hinge means comprises a living hinge in the covering between the first and second panels.

4. The apparatus of claim 1 in which the means for securing a patient to the first and second panels includes a chest strap on the first panel.

5. The apparatus of claim 1 in which the panels include foam padding.

6. The apparatus of claim 5 which the foam padding comprises a plurality of layers.

* * * * *